United States Patent [19]

Moore

[11] Patent Number: Plant 5,676

[45] Date of Patent: Mar. 4, 1986

[54] MINIATURE ROSE PLANT/VAR: MORWHY

[75] Inventor: Ralph S. Moore, Visalia, Calif.

[73] Assignee: Sequoia Nursery, Visalia, Calif.

[21] Appl. No.: 640,083

[22] Filed: Aug. 10, 1984

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized primarily by the rich red color of the open flowers which are accented by a rather large yellow "eye" with the petal reverse being yellow or yellow blend.

2 Drawing Figures

The present invention relates to a new and distinct variety of hardy, dwarf, bush type rose plant of the miniature class; the variety being primarily characterized — as to novelty — by open (7–9 petals) flowers of rich red coloring with a large yellow "eye"; the reverse (including unopened flower) being yellow or yellow blend (open flowers resemble small poppies).

The variety is further characterized by:

An abundance of bloom, with flowers borne singly or several to the stem in loose clusters.

Little or no fragrance.

A plant which is vigorous, of rounded somewhat upright shape with semi-glossy small foliage with pointed leaflets; the buds and flowers being similar in form and color (but smaller in size) to Cocktail — (shrub rose — U.S. Plant Pat. No. 1,821, expired).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Golden Angel (miniature — U.S. Plant Pat. No. 4,028) as the seed parent and an unnamed moss rose hybrid, as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety name: MORwhy (Commercial synonym: WHY NOT).

Flowers borne: Several together (3 to 5) but usually singly on slender, wirey stems.

Quantity of bloom: Abundant both outside and in greenhouse.

Bud:

*Peduncle.*—Medium to long; slender but sturdy; erect; medium to light green; hairs — numerous short hairs.

*Before calyx breaks; size.*—Small. Form long: Pointed with several soft, very short hairs and few or no foliaceous apendages on surface of bud; with foliaceous parts extending beyond the tip of the bud equal to one-half or more of its length.

*Color.*—Medium green.

*As calyx breaks, color.*—Yellow to orange — blending into, or tinted, reddish on tip portion. Opening: opens well in all weather.

Bloom:

*Size when fully open.*—Small, averaging about 30 mm ($1\frac{1}{4}$").

*Petalage.*—Single — Averaging about 7–9 petals, arranged regularly.

*Form.*—Cupped, with petals rolled loosely outward, and later at maturity open with petals remaining in similar shape and position. Open flowers show stamens.

Petals: Fairly thick; satiny on inside and on outside surface.

*Shape.*—Outside petals, broad lanceolate with rounded or very short acute tip.

Color: Newly opened flower from a plant grown in plastic greenhouse:

*Outside petal.*—Outside surface — Yellow, near Indian Yellow 6/2 on basal $\frac{1}{2}$ of petal; tip $\frac{1}{2}$ appears light red orange but this coloring is from the red portion of inside surface bleeding through the yellow. Inside surface — Near Buttercup Yellow 5/1 to 5/2 on basal $\frac{1}{2}$ of petal, thence changing into bright red, near Current Red 821/1 (with a satiny sheen). General color effect: newly opened flowers — color bright red with large yellow "eye". Three days open — Color similar to newly opened flowers but center (eye) has changed to light yellow or cream white. Behavior — Opens well in all weather. Spent petals drop off. Flower longevity (June 1984) — Plant in pot 6–8 days or longer. Cut flowers at living room temperature 5–7 days.

Reproductive organs:

*Stamens.*—Abundant, arranged regularly about pistils.

*Filaments.*—Varying length, short to medium, yellow.

*Anthers.*—Well formed; yellow.

*Pollen.*—Fair amount.

*Pistils.*—Average number.

*Styles.*—Fairly even; medium length; bunched; color — near white.

*Stigmas.*—Pale yellowish.

*Ovaries.*—All enclosed in calyx.

*Hips.*—Some — small, globe shaped.

*Sepals.*—Permanent; spear shaped; stand near upright at varying angles.

*Seed.*—Some — generally 1 seed per hip.

Foliage:

*Leaves.*—Compound of five leaflets (sometimes 3 or 7). Size — Small; leathery; semi-glossy.

*Leaflets.*—Shape: broad lanceolate; eliptical; apex acute; base rounded or rounded acute. Margin serrate. Color: Medium green; new growth — normal (medium) green, sometimes reddish or bronze (outdoors). Rachis: Medium strength; upper side may have a few tiny short hairs, grooved, underside may have 1 or 2 small hooked thorns and several small hairs. Stipules: Medium long; narrow to medium width; short length narrow points which turn out usually at about 45 degrees or more.

Growth:

*Habit.*—Dwarf; bushy; rounded; much branched.

*Growth.*—Free, vigorous; internodes short.

*Canes.*—Medium; slender; sturdy.

*Main stems.*—Color: Medium green.

*Thorns.*—Average; slender; curved, inclined slightly downward; color; dark brown. Prickles — Few or none; hairs — none.

*Branches.*—Color: light to medium green. Thorns: average; medium length; slender; generally curved, inclined slightly downward. Medium to short oval base. Prickles: few or none. Hairs: none.

*Young shoots.*—Color: light to medium green (sometimes reddish outdoors). Thorns: average, slender; generally curved, inclined slightly downward; color greenish.

The miniature rose plant and its flowers as herein described may very in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit substantially as illustrated and described, characterized by open (7–9 petals) flowers which are bright red in color, with a large yellow "eye", the reverse side of petals being yellow or yellow blend, the buds and flowers resembling the shrub rose Cocktail in form and color but smaller in size; and further characterized by a plant which is vigorous and compact, easy to propagate from soft wood cuttings or by budding, with an abundance of flowers borne singly or several to the stem in loose clusters.

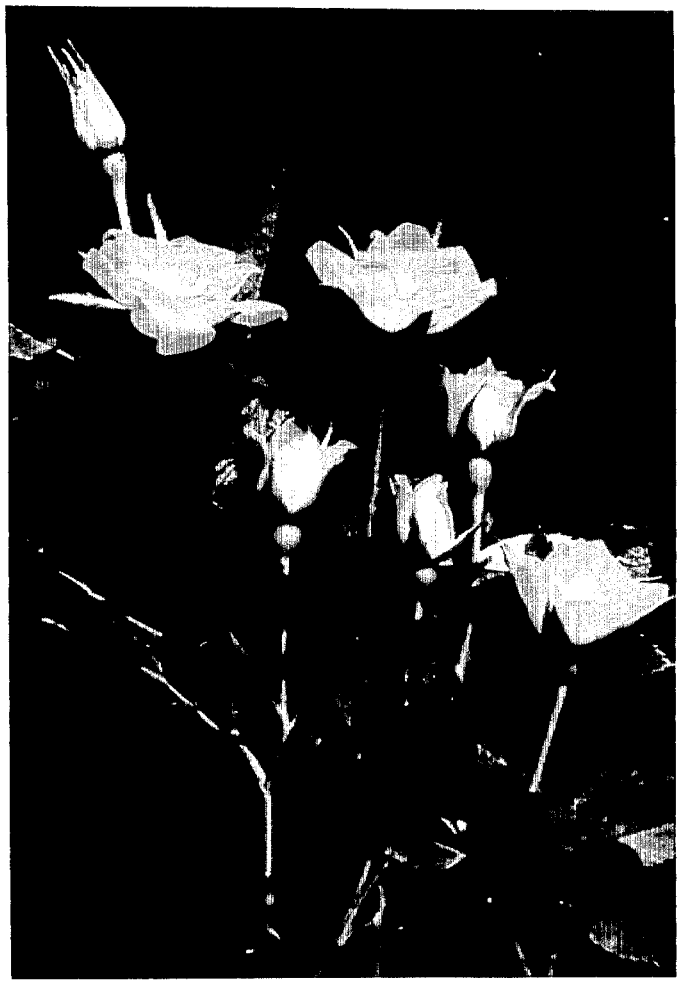
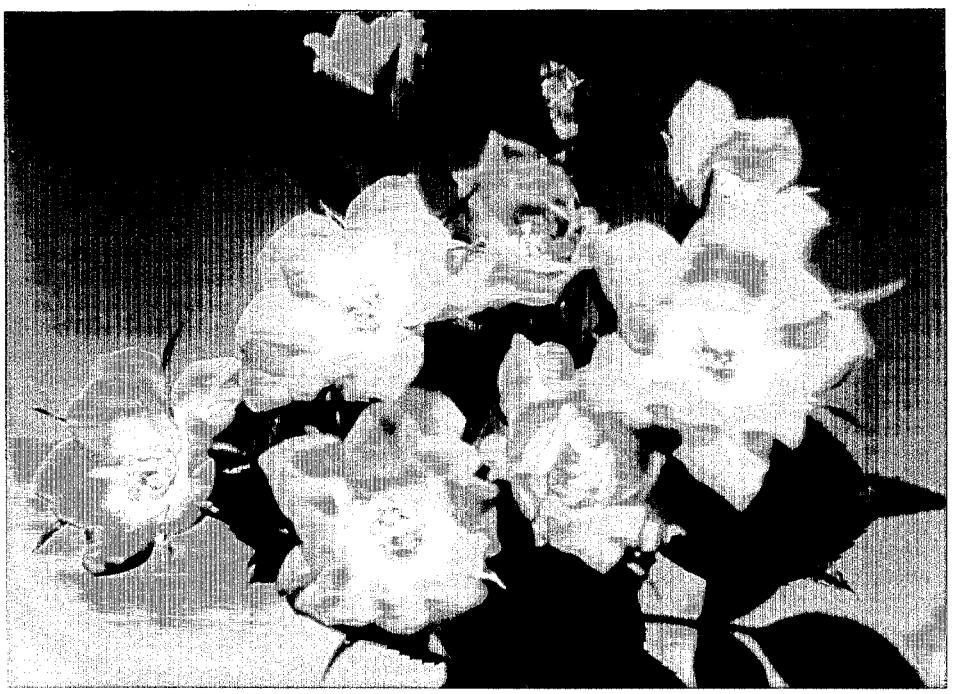

* * * * *